US00PP11522P

United States Patent [19]

Amorao et al.

[11] Patent Number: Plant 11,522

[45] Date of Patent: Sep. 26, 2000

[54] STRAWBERRY PLANT NAMED 'MONTALVO'

[75] Inventors: Amado Q. Amorao, Camarillo; Arnoldo Solis, Jr., Oxnard; Thomas M. Sjulin, Aromas; Joseph I. Espejo, Jr., Watsonville, all of Calif.

[73] Assignee: Driscoll Strawberry Associates, Inc., Watsonville, Calif.

[21] Appl. No.: 09/143,668

[22] Filed: Aug. 31, 1998

[51] Int. Cl.[7] ..... A01H 5/00

[52] U.S. Cl. ..... Plt./209

[58] Field of Search ..... Plt./209

[56] References Cited

U.S. PATENT DOCUMENTS

P.P. 5,840 12/1986 Johnson, Jr. et al. ..... Plt./209
P.P. 7,522 5/1991 Johnson, Jr. et al. ..... Plt./209

*Primary Examiner*—Howard J. Locker
*Assistant Examiner*—Wendy A Baker
*Attorney, Agent, or Firm*—Pennie & Edmonds LLP

[57] ABSTRACT

This invention relates to a new and distinct variety of strawberry named 'MONTALVO'. The variety is similar to the variety 'E26'. The variety is characterized from 'E26' by its open to medium plant density, strong plant vigor, medium to dark green leaf color, medium to strong leaf glossiness, sparse to medium petiole pubescence, few to medium number of stolons, very strong stolon anthocyanin coloration, thick stolons, smaller diameter of calyx relative to the corolla, larger diameter of inner calyx to outer calyx, medium to large fruit size, marked difference in shapes between primary and secondary fruit, medium band without achenes, level to above the surface insertion of the achenes, insertion of the calyx above the fruit, the orange red fruit flesh color, and the marginal and central distribution of the fruit flesh color.

2 Drawing Sheets

BACKGROUND OF THE INVENTION

The new variety of strawberry was discovered as a seedling in a controlled breeding plot in Ventura County, Calif., U.S.A., on or about October, 1992. The new variety originated as a result of a controlled cross between the strawberry plants named 'Mr. P' (U.S. Plant Pat. No. 5,840) and the Driscoll Strawberry Associates, Inc. variety 'R1' (unpatented) in an on-going breeding program. The original plant of this invention was asexually reproduced by stolons in a nursery in McArthur, Shasta County, Calif. Propagules were transplanted to a controlled breeding plot in Ventura County, Calif. where the claimed 'MONTALVO' variety was identified and selected for further evaluation. Clones of the new variety were further asexually propagated and extensively tested. This propagation and testing has demonstrated that the combination of traits disclosed herein which characterize the new variety are fixed and retained true to type through successive generations of asexual reproduction. 'Montalvo' differs from 'Mr. P.' being less strongly everbearing and possessing stronger plant vigor. The fruit size of 'Montalvo' is on average larger than that of 'Mr. P,' and the new variety is less susceptible to fruit bronzing than 'Mr. P.' 'R1' is a partially everbearing variety, whereas 'Montalvo' is fully everbearing. The achenes of 'R1' are more raised and more widely-spaced than those of 'Montalvo.' Lastly, the inflorescence of 'R1' branches at a lower frequency than that of 'Montalvo.'

SUMMARY OF THE INVENTION

The present invention relates to a new and distinct strawberry variety. The varietal denomination of the new variety is 'MONTVALO'. The variety is botanically identified as *Fragaria×ananassa*. Among the characteristics which distinguish the new variety from other varieties of which we are aware are a combination of traits which include plant vigor, leaf color, leaf glossiness, petiole pubescence, plant density, number of stolons, stolon anthocyanin coloration, stolon thickness, diameter of the calyx relative to the corolla of the flower, diameter of the inner calyx to the outer calyx of the flower, fruit size, difference in shape between the primary and secondary fruit, the width of the band without achenes of the fruit, insertion of achenes on the fruit, insertion of the calyx, fruit flesh color and distribution of flesh color of the fruit.

COMPARISON TO CLOSEST VARIETIES

The variety which we believe to be closest in geographic adaptation and season of ripening to 'MONTALVO' from those known to us is 'E26' (U.S. Plant Pat. No. 7,522). There are several characteristics of the new variety that are different from, or not possessed by 'E26'. For example, the plant density of 'E26' is medium to dense while that of 'MONTALVO' is open to medium dense. The plant vigor of 'MONTVALO' is strong, while that of 'E26' is medium. The leaf color of 'MONTVALO' is medium to dark green, while that of 'E26' is light to medium green. The leaf glossiness of 'MONTVALO' is medium to strong while that of 'E26' is weak. The petiole pubescence of 'MONTALVO' is sparse to medium while that of 'E26' is dense. The number of stolons of 'MONTALVO' is few to medium while that of 'E26' is medium. The stolon anthocyanin coloration of 'MONTALVO' is very strong while that of 'E26' is medium to strong. The stolon thickness of 'MONTVALO' is thick while that of 'E26' is thin to medium. The diameter of the calyx relative to the corolla of the flowers of 'MONTALVO' is smaller while that of 'E26' is the same size to larger. The diameter of the inner calyx relative to the outer calyx of the flowers of 'MONTALVO' is larger while that of 'E26' is the same size. The fruit size of 'MONTALVO' is medium to large while that of 'E26' is medium. The difference in the shape between the primary and secondary fruit of 'MONTALVO' is marked with the primary fruit being more creased and more fan shaped while the difference in shape of the fruit of 'E26' is none to very slight. The band without achenes on the fruit of 'MONTALVO' is medium while that of 'E26' is none to very slight. The insertion of the achenes on the fruit of 'MONTALVO' is level to above the fruit while that of 'E26' is below to level with the fruit. The fruit flesh of 'MONTALVO' is orange red, while that of 'E26' is pale rose. The distribution of the flesh color of the fruit of 'MONTALVO' is marginal and central while that of 'E26' is only marginal.

Regarding isozyme analysis, the phosphoglucoisomerase (PGI) isozyme banding pattern for 'MONTALVO' is A4 while that for 'E26' is A2. The leucine aminopeptidase (LAP) isozyme banding pattern for 'MONTALVO' is C4 while that for 'E26' is C2. The phosphoglucomutase (PGM) isozyme banding pattern for both 'MONTALVO' and 'E26' is B3. See *J. Amer. Soc. Hort. Sci.* 106:684 (1981).

TABLE 1

Isozyme Phenotypes for 'MONTALVO' and 'E26'

| | Cultivar | |
|---|---|---|
| Locus | 'MONTALVO' | 'E26' |
| PGI | A4 | A2 |
| LAP | C4 | C2 |
| PGM | B3 | B3 |

The isozyme data for 'E26' is from U.S. Plant Pat. No. 7,522 and its Certificate for Correction (incorporated herein by reference).

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
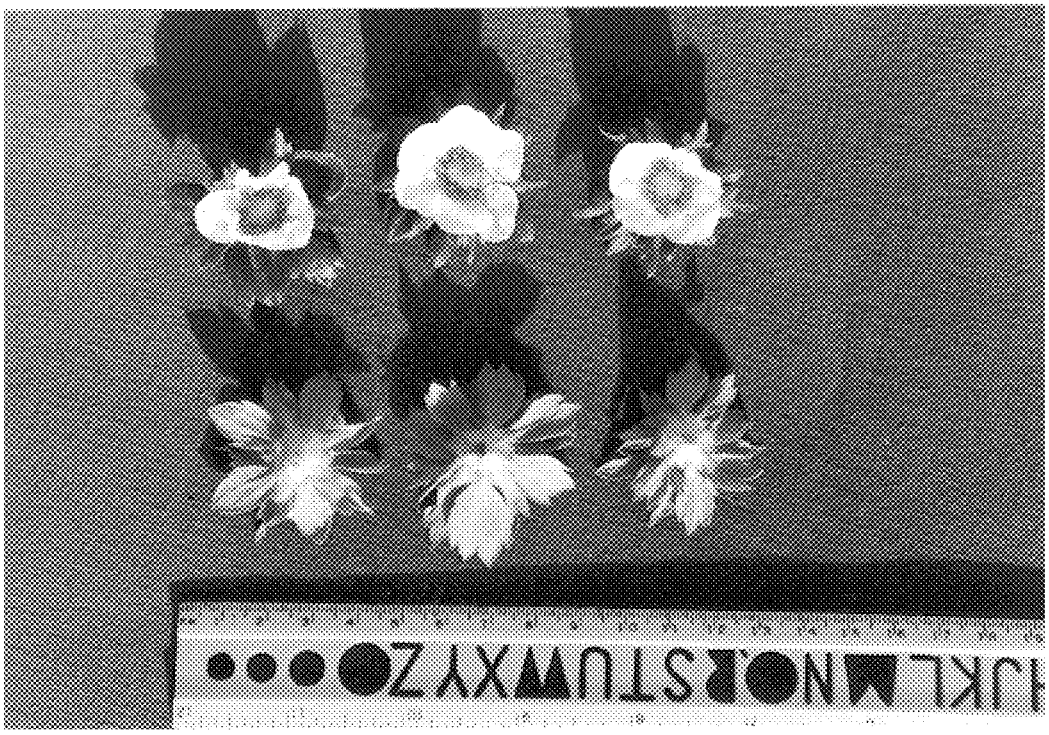
FIG. 1 shows the flower and reproductive organs of the new variety, as well as the size and position of the petals and sepals and the underside of the calyx.
Figure 2:
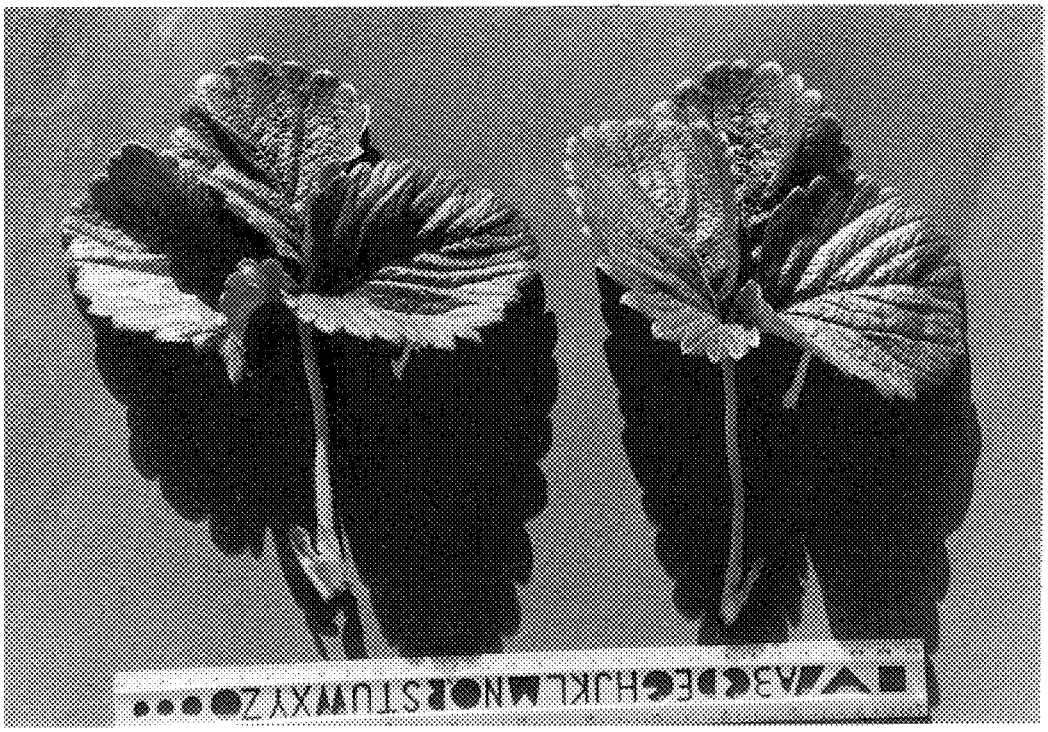
FIG. 2 shows the upper surface of two typical folioles of the new variety.
Figure 3:
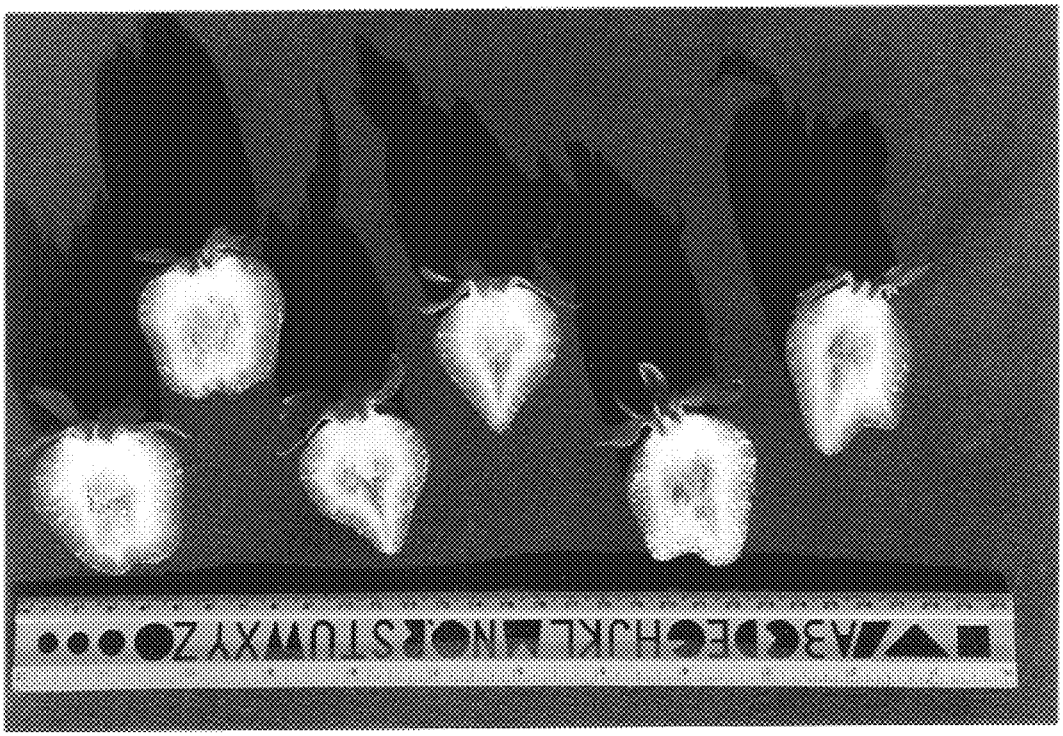
FIG. 3 shows the fruit in longitudinal section and cross section, illustrating the typical flesh and flesh coloration.
Figure 4:
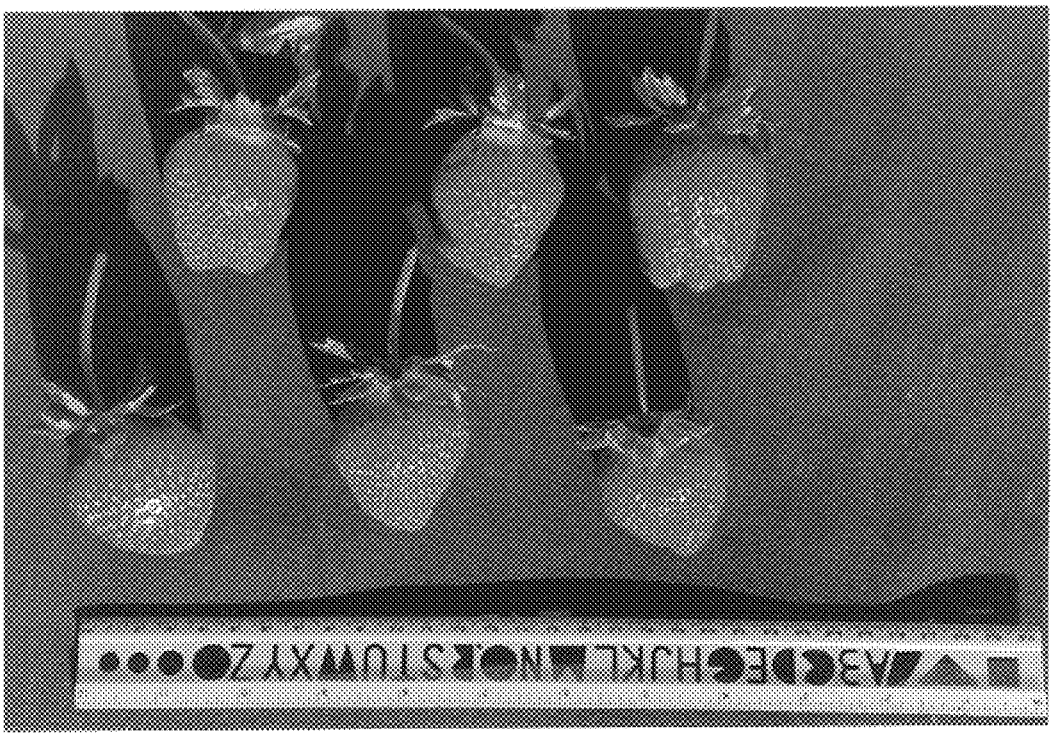
FIG. 4 shows typical whole fruit.

The following detailed description of the new variety is based upon observations taken of plants and fruit grown in experimental test plots in Ventura County, Calif., U.S.A. The plant material was planted in July, 1997 in a summer plant system. Observations of 'MONTALVO' and 'E26' were taken in side by side comparison in the fall of 1997. This description is in accordance with UPOV terminology. Color designations, color descriptions, and other phenotypical descriptions may deviate from the stated values and descriptions depending upon variation in environmental, seasonal, climatic and cultural conditions. Colors are described using The Royal Horticultural Society (R.H.S.) Colour Chart.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant:
- *Habit.*—Flat globose.
- *Density.*—Open to medium.
- *Vigor.*—Strong.
- *Height of plant.*—25.6 cm.
- *Diameter of plant.*—40.4 cm.
- *Number of crowns plant.*—3.0.

Foliage:
- *Leaf.*—Color of Upper Side — 147A (light to medium green). Color of Under Side — 138C (light gray green). Shape in cross section — flat to slightly convex. Blistering — strong. Number of leaflets — three only. Leaf glossiness — medium to strong.
- *Terminal leaflet margin.*—Profile — revolute. Length to width ratio — as long as broad. Terminal Leaflet Length — 9.5 cm. Terminal Leaflet Width — 9.6 cm. Terminal Leaflet Length/Width Ratio — 0.98. Number of Teeth/Terminal Leaflet — 20.6. Shape of base — obtuse. Shape of teeth — rounded.
- *Petiole.*—Pubescence — sparse to medium. Pose of hairs — outwards to downwards.
- *Petiole length.*—15.4 cm.
- *Petiole color.*—144C (yellow-green).
- *Bract frequency.*—17%, Typically Single.
- *Stipule length.*—3.5 cm.
- *Stipule width.*—1.2 cm.
- *Stipule color.*—145A (yellow-green).
- *Stolons.*—Number — few to medium in number. Anthocyanin coloration — very strong. Thickness — thick. Pubescence — medium.
- *Inflorescence.*—Position relative to foliage — beneath to level with.

Flower: The flowers described are secondary flowers except where indicated.
- *Size.*—Medium. Average diameter of flowers for 'MONTALVO' is 26.5 mm. Average diameter of the calyx of 'MONTALVO' is 26 mm.
- *Diameter of calyx relative to corolla.*—(Secondary flowers) smaller.
- *Diameter of inner calyx relative to outer* (*on secondary flowers*).—Larger.
- *Spacing of petals* (*on secondary flowers with* 5 *or* 6 *petals*).—Touching to overlapping.
- *Petal.*—'MONTALVO'.
- *Average length.*—10.2 mm.
- *Average width.*—10.5 mm.
- *Petal length to width ratio* (*on secondary flowers*). —0.97.
- *Flower shape.*—Typical of the species.
- *Petal Color.*—155D (white).
- *Fragrance.*—None.
- *Average number of sepals.*—10 (sepals are free from the petals and fruit.)
- *Fruiting truss.*—Attitude at first picking — semi-erect. Length — medium.

Fruit: (Secondary fruit on one year old plants) All fruit characteristics are similar between primary and secondary fruit, unless specified. Ratio of length to maximum width — as long as broad to longer than broad.
- *Size.*—Seconary fruit — medium to large. The fruit of 'MONTALVO' average 19.0 g/fruit while that of 'E26' average 17.8 g/fruit.

*Predominant shape.*—Conical to biconical.

*Difference in shapes between primary and secondary fruits.*—Marked with the primary fruit being more creased and more fan-shaped.

*Band without achenes.*—(Secondary fruit) — medium.

*Unevenness of surface.*—(Secondary fruit) weak to medium.

*Skin color*—42A (orange red).

*Evenness of color.*—Slightly uneven to even.

*Glossiness.*—Strong.

*Insertion of achenes.*—Level to above the surface.

*Insertion of calyx.*—Set above the fruit.

*Pose of the calyx segments.*—Spreading to reflexed.

*Size of calyx in relation to corolla.*—Primary Flowers — same size to larger. Secondary Flowers — smaller.

*Adherence of calyx* (*when ripe for fresh market*). — Medium to strong.

*Firmness of flesh* (*when fully ripe*).—Medium.

*Evenness of color of flesh.*—Slightly uneven.

*Distribution of flesh color.*—Marginal and central.

*Hollowness of center.*—Absent to small.

*Sweetness.*—Medium.

*Texture when tasted.*—Fine.

*Acidity.*—Medium.

*Color of fruit flesh-center.*—40A (orange).

*Color of fruit flesh-vascular tissue.*—155A (white).

*Color of fruit flesh-margin of berry.*—43A (orange-red).

*Color of calyx.*—138B (green).

*Color of achenes.*—13A to 26 A (yellow to orange).

*Fruit quality.*—% Brix — 9.0. Titratable acidity — 7.88 mg/g citric acid equivalents. Penetrometer Reading — N/A.

Time of flowering (50% of plants at first flower): Early. Initial flowering occurs around September 1, approximately four weeks after planting.

Harvest maturity (50% of plants with ripe fruit): Early.

Type of bearing: Fully everbearing. The variety is grown under a short cycle cropping system that does not allow two major cropping periods.

Season of harvest: The season of harvest for 'MONTALVO' in Ventura County, Calif. in 1997 was approximately from the week of October 4 to the week of December 6.

Cultural practices: 'MONTALVO' is best adapted to a summer plant system in southern California. Plants of 'MONTALVO' that have been stored for 4–6 months at −1° C. are planted in the summer months and fruit during the fall and early winter of the same year.

Shipping and storage characteristics: The shelf life of 'Montalvo' as measured by the amount of fruit damage following prolonged storage at 34° is superior to that of 'E26' and inferior to that of 'Baeza'. The average shelf life ratings on a 1 to 10 scale for 'E26,', 'Montalvo,' and 'Baeza' were 5.5, 6.7, and 8.0, respectively.

Resistance to Stress

The new variety is moderately resistant to drought and high temperatures. The new variety is moderately susceptible to wind and water logging. The new variety is susceptible to high pH and high soil salt levels.

Insect and Disease Resistance and Susceptibility

The 'MONTALVO' variety is moderately susceptible to *Tetranychus urticae*. 'MONTALVO' is susceptible to Aphis spp. 'MONTALVO' variety is moderately resistant to the Strawberry Mottle Virus and *Xanthamonas fragariae*. 'MONTALVO' is moderately susceptible to leaf spots (*Ramularia tulasnei*), powdery mildew and Botrytis fruit rot. 'MONTALVO' is susceptible to Verticillium wilt.

What is claimed is:

1. A new and distinct variety of strawberry plant, substantially as shown and described.

* * * * *